(12) United States Patent
Gergely (10) Patent No.: US 12,278,008 B2
(45) Date of Patent: Apr. 15, 2025

(54) THERAPEUTIC SYSTEM AND METHOD FOR TEACHING SOCIAL OR EMOTIONAL MANAGEMENT SKILLS TO A PATIENT

(71) Applicant: Erica Jex Gergely, Indianapolis, IN (US)

(72) Inventor: Erica Jex Gergely, Indianapolis, IN (US)

( * ) Notice: Subject to any disclaimer, the term of this patent is extended or adjusted under 35 U.S.C. 154(b) by 340 days.

(21) Appl. No.: 18/100,036

(22) Filed: Jan. 23, 2023

(65) Prior Publication Data

US 2024/0249820 A1      Jul. 25, 2024

(51) Int. Cl.
  *G16H 20/70*      (2018.01)
  *G16H 80/00*      (2018.01)

(52) U.S. Cl.
  CPC ............. *G16H 20/70* (2018.01); *G16H 80/00* (2018.01)

(58) Field of Classification Search
  CPC ............................... G16H 20/70; G16H 80/00
  See application file for complete search history.

(56) References Cited

U.S. PATENT DOCUMENTS

| | | | |
|---|---|---|---|
| 5,405,266 | A | 4/1995 | Frank et al. |
| 6,890,239 | B2 | 5/2005 | Kopelle |
| 8,909,370 | B2 | 12/2014 | Stiehl et al. |
| 9,814,993 | B2 | 11/2017 | Ponomarev et al. |
| 10,360,810 | B1 | 7/2019 | Horowitz et al. |
| 11,185,659 | B2 | 11/2021 | Kalensky |
| 2007/0128979 | A1 | 6/2007 | Shackelford et al. |
| 2018/0213951 | A1* | 8/2018 | Newman ................ B42D 15/02 |
| 2019/0224444 | A1* | 7/2019 | Kalensky ................. A63H 3/28 |
| 2025/0025662 | A1* | 1/2025 | Cronin ..................... A63H 3/02 |

FOREIGN PATENT DOCUMENTS

| | | | | |
|---|---|---|---|---|
| DE | 202006021211 U1 | * | 2/2014 | ............ A63H 3/365 |
| JP | 2002172274 A | * | 6/2002 | |
| JP | 2018117821 A | * | 8/2018 | |
| KR | 20220088535 A | * | 6/2022 | ............ H05B 45/20 |

OTHER PUBLICATIONS

DE-202006021211-U1—translated (Year: 2014).*
JP-2002172274-A—translated (Year: 2002).*
KR-20220088535-A—translated (Year: 2022).*
JP-2018117821-A—translated (Year: 2018).*

* cited by examiner

*Primary Examiner* — Jason S Tiedeman
*Assistant Examiner* — Camryn B. Lewis
(74) *Attorney, Agent, or Firm* — H. Brock Kolls (57) ABSTRACT

The present invention relates to a therapeutic system and method for teaching social and emotional management skills to patients. Instructive messages that teach self-soothing skills to mitigate social and emotional conditions are encoded into a plushy. At the onset of one of the social and emotional conditions, in a patient, the patient interacts with the plushy, listens to the appropriate instructive message, and physically implements the self-soothing skill to mitigate the social and emotional condition. A caregiver can encode a situational message in the plushy that is appropriate for the situational environment the patient is within. Therapist messages can be encoded in the plushy to determine the patient's treatment plan progress. The treatment plan continues until, at the onset of a social or emotional condition, in the absence of the plushy, the patient physically implements the self-soothing skill to mitigate the social or emotional condition. The plushy can be web-enabled.

21 Claims, 5 Drawing Sheets

Fig. 5

THERAPEUTIC SYSTEM AND METHOD FOR TEACHING SOCIAL OR EMOTIONAL MANAGEMENT SKILLS TO A PATIENT

TECHNICAL FIELD OF THE INVENTION

This invention relates to a therapeutic system and method for teaching patients social and emotional management skills. Instructive messages that teach self-soothing skills to mitigate social and emotional conditions are encoded into a plushy. At the onset of one of the social and emotional conditions, in the patient, the patient interacts with the plushy, listens to the appropriate instructive message, and physically implements the self-soothing skill to mitigate the social and emotional condition. The treatment plan continues until, at the onset of a social or emotional condition, in the absence of the plushy, the patient physically implements the self-soothing skill to mitigate the social or emotional condition.

BACKGROUND OF THE INVENTION

Before our invention when a child acted out or became hyper-emotional at seemingly the smallest things, a shortcoming was that caregivers had few options to resolve the matter. Attempts could be made to calm the child, but the child had no way to learn how to self-soothe themselves to return to a calm state.

Such disruptions, by an unruly child in places like home, school, restaurants, airplanes, and other places can be untimely, unpredictable, and paralyzing to parents, family members, teachers, and other people located in proximity to the commotion.

Absent a therapy solution to allow children to learn how to self-mitigate their own social and emotional conditions to return to a calm state, shortcomings and prior attempts to remedy volatile situations by de-escalating a hyper-emotional child largely fell to caregivers who often as a first and last resort used forms of punishment such as sending them to their room, removing them from a classroom, grounding or removing privileges, placing them in timeout, and so on.

The present invention addresses these and other shortcomings by providing a therapeutic system and method for teaching patients social or emotional management skills. For these reasons and shortcomings as well as other reasons and shortcomings there is a long-felt need that gives rise to the present invention.

SUMMARY OF THE INVENTION

The shortcomings of the prior art are overcome and additional advantages are provided through the provision of a therapeutic system for teaching social and emotional management skills to a patient. The system comprises at least one instructive message that teaches a self-soothing skill that a patient physically implements and a patient treatment plan for one or more social or emotional conditions. The patient treatment plan comprises one or more instructive messages selected based in part on the self-soothing skill desired to counteract at least one identified social or emotional condition.

The therapeutic system further comprises an electronic control system. The electronic control system comprises a microcontroller, a memory, one or more sensor input, an amplifier, and a speaker. The memory, the sensor input, and the amplifier are operationally related to the microcontroller. The speaker is operationally related to the amplifier. The memory is encoded with each of the instructive messages and played by way of the speaker when the patient triggers at least one of the sensor inputs. Each of the instructive messages is associated with specific one or more sensor inputs.

The therapeutic system further comprises a plushy that implements a portion of the patient treatment plan as the patient interacts with the plushy. The plushy comprises an electronic control system. Each time the patient feels the onset of one of the social or emotional conditions, the patient triggers appropriate one or more of the sensor inputs, listens to the instructive message, and physically implements the self-soothing skill to mitigate the social or emotional conditions. Wherein the patient's treatment plan continues over a treatment period until responsive to the onset of the social or emotional condition, in the patient, the patient physically implements the self-soothing skill, mitigating the social or emotional condition, in the absence of the patient interacting with the plushy.

Additional shortcomings of the prior art are overcome and additional advantages are provided through the provision of a therapeutic method for teaching social and emotional management skills to a patient. The method comprises the steps of purchasing a plushy. The plushy implements a portion of a patient treatment plan for one or more social or emotional conditions as a patient interacts with the plushy. The patient treatment plan comprises one or more instructive messages selected based in part on a self-soothing skill desired to counteract at least one of the identified social or emotional conditions. The instructive message teaches the self-soothing skill that the patient physically implements.

The method further comprises the step of encoding a memory with each of the instructive messages. An electronic control system comprises a microcontroller, memory, one or more sensor input, an amplifier, and a speaker. The memory, the sensor input, and the amplifier are operationally related to the microcontroller, the speaker is operationally related to the amplifier. The plushy comprises an electronic control system.

The method continues by playing, each time the patient feels the onset of one of the social or emotional conditions, at least one instructive message by way of the speaker when the patient triggers the appropriate one or more sensor inputs. Each of the instructive messages is associated with one or more of the sensor inputs. The method continues by mitigating the social or emotional condition by the patient listening to the instructive message, and physically implementing the self-soothing skill taught by the instructive message.

Additional shortcomings of the prior art are overcome and additional advantages are provided through the provision of a therapeutic method for teaching social and emotional management skills to a patient. The method comprises the steps of identifying a patient with at least one social or emotional condition that requires mitigation and determining a patient treatment plan for one or more of the social or emotional conditions. The patient treatment plan comprises one or more instructive messages selected based in part on a self-soothing skill desired to counteract at least one of the identified social or emotional conditions. The instructive message teaches the self-soothing skill that the patient physically implements.

The method further comprises the step of encoding a memory with each of the instructive messages. An electronic control system comprises a microcontroller, memory, one or more sensor inputs, an amplifier, and a speaker. The memory, the sensor input, and the amplifier are operationally related to the microcontroller. The speaker is operationally related to the amplifier.

The method continues by allowing the patient to interact with a plushy. The plushy implements a portion of the patient treatment plan for one or more of the social or emotional conditions as the patient interacts with the plushy. The plushy comprises an electronic control system.

The method continues by playing, each time the patient feels the onset of one of the social or emotional conditions, at least one instructive message by way of the speaker when the patient triggers appropriate one of the sensor inputs. Each of the instructive messages is associated with one or more of the sensor inputs. The method continues by mitigating the social or emotional condition, by the patient listening to the instructive messages and physically implementing the self-soothing skills taught by the instructive messages.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

Many people suffer from social or emotional conditions such as anger, fear, anxiety, depression, disruptive behavior, dissocial disorder, post-traumatic stress disorder, or other social or emotional conditions. In children, such disorders often manifest as big emotional outbursts at home, school, out in public, and in other places. Such social or emotional conditions can be particularly difficult for children to contend with simply because they lack the social or emotional management skills to understand and self-mitigate highly charged situations that from time to time, they find themselves within.

In the present invention, an advantage is that a patient can be trained to self-soothe and calm themselves through triggering situations to mitigate social or emotional conditions. In this regard, through the use of evidence-based instructive messaging that teaches the patient self-soothing skills delivered through a plushy, the patient upon onset of a triggering event is instructed to physically implement a self-soothing skill. Such self-soothing skills can include instructing patient 302 to touch, observe, or smell something in their environment, perform a breathing exercise, or other types and kinds of self-soothing skills that can be physically implemented by the patient.

Unique in this approach is that the patient is taught self-soothing skills allowing treatment progress to be measured in at least two different ways. First, access to the plushy can be removed and the patient tested to see if they self-implement one of the self-soothing skills on their own, absent the plushy, to mitigate a triggering event. And second, during a therapy session, the plushy can play different therapy messages that engender the patient to teach one or more self-soothing skills to the plushy in response to the therapist creating hypothetical triggering situations the plushy finds itself.

The term "plushy", in the present invention, is intended to mean a stuffed toy such as a teddy bear or other object that a patient can develop a rapport with as a means to facilitating a patient treatment related to treating social or emotional conditions. The patient treatment plan is inclusive of a plushy that interacts with the patient by playing instructive messages that teach a self-soothing skill selected based in part on one or more social or emotional conditions the patient is encountering, situational messages programmable or otherwise recordable by a caregiver that is unique to the patient's environment or situational surroundings, or therapist messages that are played when the patient interacts with a therapist.

A caregiver can be a parent, guardian, teacher, babysitter, family friend, grandparents, doctor, counselor, family member, or other relevant persons who interact with the patient and has an obligation to promote their well-being.

In the present invention, the term "triggering" is intended to mean some event or occurrence that causes the onset of one or more social or emotional conditions in the patient. Such triggering often manifests as a display, by the patient, of exaggerated or big emotional outbursts, abrupt personality/mood changes, and/or present in other ways.

The term "therapy messages", in the present invention, is intended to mean messages 812 selected by a therapist 304 and encoded in the plushy 400 that the plushy 400 plays during a therapy session with a therapist 304, responsive to the patient 302 interacting with and triggering one or more of the sensor inputs 612 on the plushy 400. Such therapy messages are intended to facilitate interactions between therapist 304, patient 302, and plushy 400 that will inform the therapist of the patient's 303 patient treatment plan 802 progress by allowing the patient to teach the plushy self-soothing skills in response to therapist-created hypothetical situations aid by the therapy messages.

The term, "situational message", in the present invention, is intended to mean messages 810 selected by a caregiver 306 and encoded in the plushy 400 that the plushy 400 plays responsive to the patient 302 interacting with and triggering one or more of the sensor inputs 612 on the plushy 400 in certain environmental situations such as school, work, doctor appointments, or other situational environments. In this regard, situational messages 810 allow caregiver 306 to customize the plushy 400 with a situational message to be relevant to the situational environment that patient 402 encounters or is otherwise within. The situational message 810 can be changeable by caregiver 306 or other authorized persons to adapt to patient 302 transitioning into different situational environments.

Figure 1:
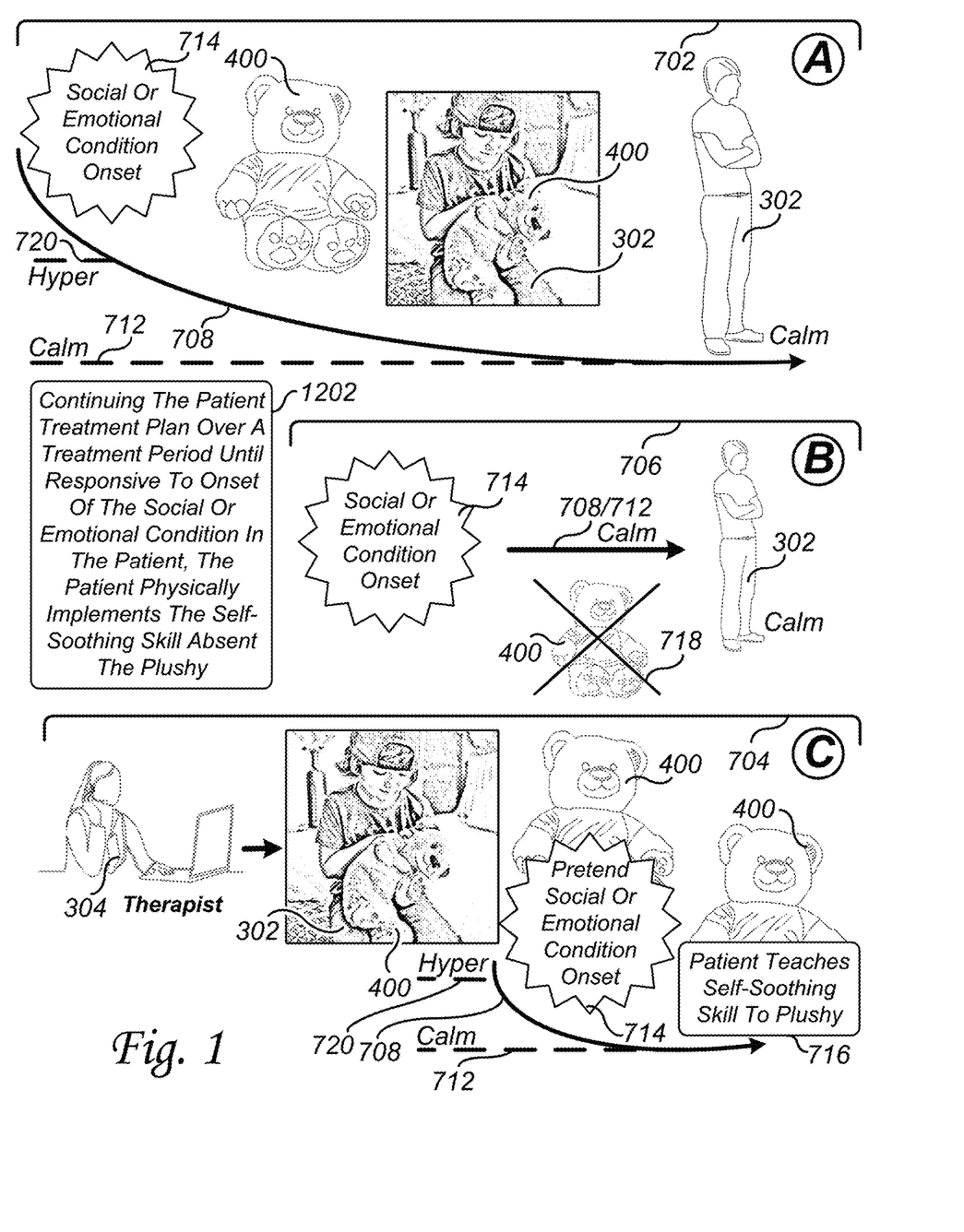
FIG. 1 illustrates one example of an approach to teaching social and emotional management skills to a patient.

Turning now to the drawings in greater detail, it will be seen that in FIG. 1 there is one example of an approach to teaching social and emotional management skills to patient 302. In operation, in an exemplary embodiment, in reference 'A' 702, when patient 302 encounters the onset of a social or emotional condition 714 an initial escalation of emotions or actions can quickly create a hyper-emotional situation 708/720 for both patient 302 and the people around the patient 302. The hyper-emotional situation 708 curve is an illustrative tool to indicate a patient's hyper, soothing, or calmed state, being initially elevated as hyper 720, in this example, with the onset of a social or emotional condition event trigger 714 and calming 712 in accordance with the patient treatment plan 802 and action by the patient interacting with plushy 400.

In this regard, responsive to the hyper-emotional situation 708/720 and in accordance with the patient treatment plan 806, an encoded evidenced-based instructive message 806 in a memory 620 that is part of an electronic control system 600. The electronic control system 600 is embedded in a plushy 400. The plushy 400 is made accessible to an agitated patient 302. The patient engages with the plushy 400 to start the reduction of the hyper-emotional situation 708. Patient 302 presses or otherwise triggers one or more of the sensor inputs 612/618, listens to an instructive message 806 that teaches a self-soothing skill further calming the hyper-emotional situation 708, and then physically implements the self-soothing skill learned from the instructive message 806 self-soothing patient 302 restoring and returning the patient to a calm state 712.

Each of the instructive messages 806 teaches a self-soothing skill that patient 302 physically implements. The self-soothing skills can be selected based on the type and kind of social or emotional conditions patient 302 is experiencing. As an example, and not a limitation, such instructive messages 806 can include asking patient 302 to look around the room and tell me what you can see, hear, smell, or feel. Other instructive messages 806 can include asking patient 302 to find something in the room to smell or touch, or asking patient 302 to describe how they feel in a particular situation. Other instructive messages 806 can include asking patient 302 to sniff an imaginary flower or blow up an imaginary balloon or asking patient 302 to perform a deep breathing exercise, or other types and kinds of instructive messages that teach patient 302 self-soothing skills, as may be required and/or desired in a particular embodiment.

In the present invention, as illustrated in reference 'B' 706 and method step 1202 which can be used interchangeably with the methods of the present invention, an advantage is that the patient treatment plan 806 continues over a treatment period until responsive to the onset of the social or emotional condition 804, in patient 302, patient 302 physically implements one of the learned self-soothing skills to mitigate the social or emotional condition 804, in the absence 718 of patient 302 interacting with the plushy 400. This indicates that patient 302 has learned the soothing skills and knows how to apply them to the onset of triggering social or emotional situations to self-soothe and maintain or return to a calm state without the need to listen to an instructive message 806. In this regard, patient treatment plan 802 progress and success can be tracked or otherwise measured when in the presence of what would be a triggering hyper-emotional situation 708 patient 302 implements one of the self-soothing skills in the absences of the plushy 400 to maintain or return to a calm and soothe state 712.

In an exemplary embodiment, such a treatment period can range from days to weeks to years depending on the nature of the social or emotional conditions 804, the interaction time between patient 302 and plushy 400, and other factors.

In an exemplary embodiment, the present invention is a system for teaching social and emotional management skills to patient 302, the system comprises at least one instructive message 806 that teaches a self-soothing skill that patient 302 physically implements.

The system further comprises a patient treatment plan 802 for one or more of a social or emotional condition 804. The patient treatment plan 802 comprises one or more of the instructive messages 806 selected based in part on the self-soothing skill desired to teach patient 302 to counteract at least one of the identified social or emotional conditions 804.

Figure 4:
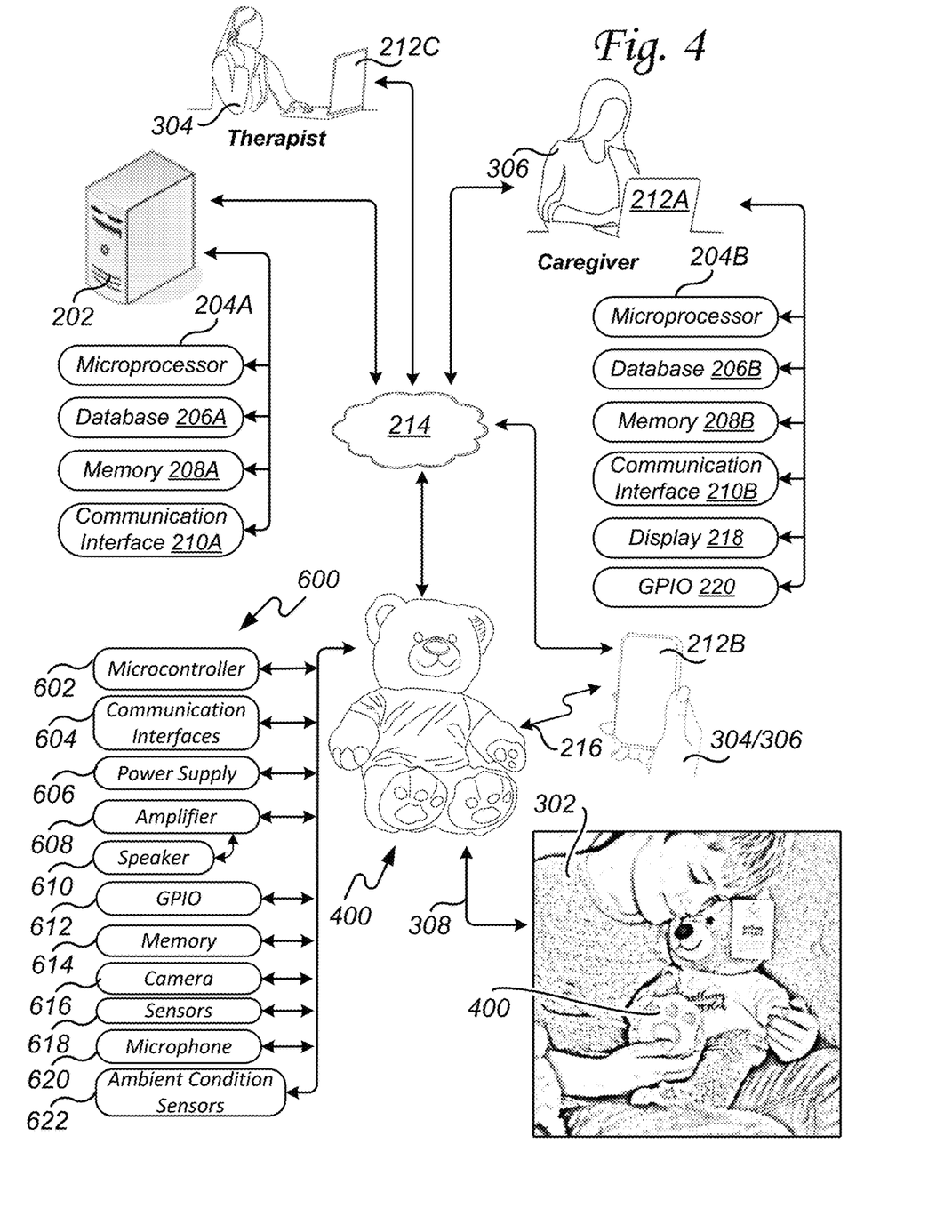
FIG. 4 illustrates one example of a therapeutic system for teaching social and emotional management skills to a patient.

The system further comprises an electronic control system 600, the electronic control system 600 comprises a microcontroller 602, a memory 614, and one or more sensor inputs 612/618 which can be implemented with general purpose inputs and outputs (GPIO) 612 or sensors 618, an amplifier 608, and a speaker 610. The memory 614, the sensor input 612/618, and the amplifier 608 are operationally related to the microcontroller 602. Speaker 610 is operationally related to amplifier 608. Memory 614 is encoded with each of the instructive messages 806 and played by way of speaker 610 when patient 302 triggers at least one of the sensor inputs 612/618. Each of the instructive messages is associated with one or more of the sensor inputs 612/618 allowing patient 302 to play a desired instructive message each time the same sensor input 612/618 is triggered by patient 302. In this regard, patient 302 can listen to the instructive 806 of their choice.

In other exemplary embodiments, some or all of the instructive message 806 can be randomly played when certain or all of the sensor inputs 612/618 are triggered by patient 302. In this regard, patient 302 is exposed to all of the instructive messages taught self-soothing skills in a semi-equal manner.

The system further comprises a plushy 400 that implements a portion of the patient treatment plan 802 as patient 302 interacts with the plushy 400. The plushy 400 comprises the electronic control system 600. In this regard, each time patient 302 feels the onset of one of the social or emotional conditions 804, patient 302 triggers the appropriate one or more of the sensor inputs 612/618, listens to the instructive message 806, and physically implements the self-soothing skill to mitigate the social or emotional condition 804. The patient treatment plan 802 continues over a treatment period until responsive to the onset of a social or emotional condition 804, in patient 302, patient 302 physically implements the learned self-soothing skill to mitigate the social or emotional condition 804, in the absence 718 of the patient 302 interacting with the plushy 400 to listen to one of the instructive messages 806.

With reference to FIG. 1 reference 'C' 704, in an exemplary embodiment, one or more therapy session messages 812 can be encoded in memory 614 and played by way of the speaker 610 during a therapy session between therapist 304 and patient 302 when patient 302 triggers one of the sensor inputs 612/618. In this regard, therapy session message 812 instructs patient 302 to teach one or more of the self-soothing skills learned from the instructive messages

806 to plushy 400 so that therapist 304 can evaluate the progress of patient 302 and the effectiveness of the patient treatment plan 802.

In operation, therapist 304 and patient 302 engage in a therapy session in person or virtually. Responsive to therapist 304 presenting to patient 302 a pretend or hypothetical social or emotional condition onset 714 to create a pretend or hypothetical hyper-emotional situation 708/720 that plushy 400 is experiencing (not the patient 302), patient 302 responds by teaching 716 plushy 400 one or more of the self-soothing skills patient 302 has learned to return plushy 400 to a calm 708/712 state. Therapy messages 812 can be used to enable plushy 400 to communicate with patient 400. In this regard, therapist 304 can evaluate how patient 302 handles plushy's 400 hypothetical social or emotional condition onset 708/714/720 and intervenes to teach 716 plushy 400 self-soothing skills that patient 302 has previously learned through the patient treatment plan 802 and prior interaction with plushy 400 in patient 302 real-world situations.

Figure 2:
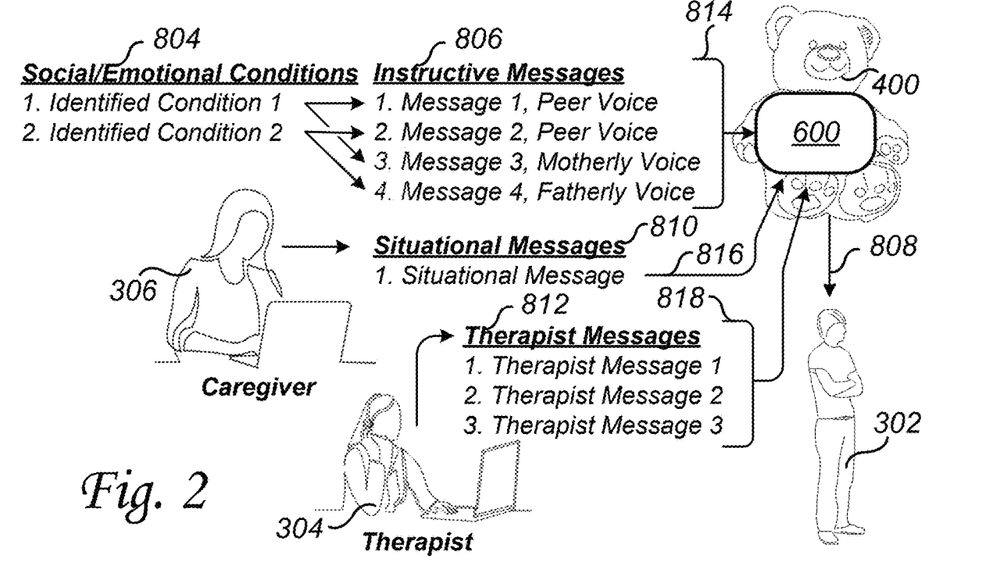
FIG. 2 illustrates one example of a therapeutic method for teaching social and emotional management skills to a patient.

Referring to FIG. 2, there is illustrated one example of a method of teaching social and emotional management skills to a patient. In an exemplary embodiment, patient 320 can be identified with one or more social or emotional conditions 804. Such identification can be by way of a therapist 304, a caregiver 306, a doctor, a counselor, the patient 302 themself, or other persons.

In an exemplary embodiment, an additional step of identifying can comprise a person, such as a caregiver or other person, using an online software tool to determine one or more of the social or emotional condition 802 that requires mitigation in a patient 302. Such an online software tool can be a questionnaire, a frequently asked question (FAQ), a telemedicine or teletherapy session with a therapist or other authorized person, an informational blog, audio, podcasts, videos, or other online software tools as may be required and/or desired in a particular embodiment.

Once the social or emotional conditions 804 are determined, instructive messages 806 can be selected based in part on a self-soothing skill desired to counteract the identified social or emotional conditions 804. Each of the instructive messages 806 teaches a self-soothing skill. Such instructive messages 806 can be encoded 814 in memory 614 by physically recording with a microphone 620, encoding on a memory 614 that is permanently affixed within the electronic control system 600, encoding on a removable memory 614 (such as a USB flash drive, or other removable memory) and inserted into the electronic control system 600, the instructive messages 806 can be locally or remotely digitally downloaded to the electronic control system 600, or the instructive messages 806 can be encoded 814 in the electronic control system 600 in other suitable ways.

In an exemplary embodiment, adolescent patients 302 can be more receptive to certain instructive messages 806 being spoken, from plushy 400, in a peer voice, that is by someone of similar age and/or gender as patient 302, and certain of the instructive messages 806 being spoken, from plushy 400, by an adult motherly voice or an adult fatherly voice. In operation, a plurality of instructive messages 806 can comprise patient peer voices, motherly voices, and/or fatherly voices as may be required and/or desired in a particular embodiment.

In this regard, at least one of the instructive messages 806 can be recorded in a peer voice by someone of similar age and/or gender as patient 302, and at least one of the instructive messages 806 can be recorded in a motherly voice by an adult female or a fatherly voice by an adult male.

In an exemplary embodiment, since patients 302 are often engaged with a caregiver 306 during daily routines there can be situations and physical environments that a customized situational message 810 can be helpful as a part of the patient's 302 treatment. In this regard, at least one of the messages can be at least one situational message 810 that is encoded 816 in memory 614 which is played by way of speaker 610. The situational messages 810 can be recorded by microphone 620, encoded on removable memory 614 and inserted into the electronic control system 600, downloaded from a local computing device 212 or remote data processing resource 202, or encoded in the electronic control system 600 in other ways by a caregiver 306 or other authorized persons. Situational message 810 is an instructive message that relates to the situational environment around patient 302. The situational message 810 can be changeable by caregiver 306 or other authorized persons to adapt to patient 302 transitioning into different situational environments.

In an exemplary embodiment, one or more therapy messages 812 can be encoded 818 in memory 614 and played by way of the speaker 610 only during a therapy session between therapist 304 and patient 302 when patient 302 triggers one of the sensor inputs 612/618. In this regard, therapy session message 812 instructs patient 302 to teach one or more of the self-soothing skills learned from the instructive messages 806 to the plushy 400 so that therapist 304 can evaluate the treatment progress of patient 302. The therapist messages 812 can be encoded 818 in memory 614. Such therapist messages 812 can be encoded 814 in memory 614 by physically recording with a microphone 620, encoding on a memory 614 that is permanently affixed within the electronic control system 600, encoding on a removable memory 614 (such as a USB flash drive, or other removable memory) and inserted into the electronic control system 600, the instructive messages 806 can be locally or remotely digitally downloaded to the electronic control system 600, or the therapist messages 812 can be encoded 814 in the electronic control system 600 in other suitable ways.

In an exemplary embodiment, once the plushy 400 has been encoded with the instructive messages 806, optional situational messages 810, and optional therapist messages 812 the plushy 400 is given 808 to or otherwise used with patient 302 as part of a patient treatment plan 802.

In an exemplary embodiment, the method begins in step 1002 with a plushy 400 being purchased, the plushy 400 implements a portion of a patient treatment plan 802 for one or more of a social or emotional condition 804 as a patient 302 interacts with the plushy 400. The patient treatment plan 802 comprises one or more of an instructive message 806 selected based in part on a self-soothing skill desired to counteract at least one of the identified social or emotional conditions 804. The instructive message teaches the self-soothing skill that patient 302 physically implements. The method then moves to step 1004.

In step 1004, memory 614 is encoded 814 with each of the instructive messages 806. An electronic control system 600 comprises a microcontroller 602, the memory 620, one or more sensor inputs 612/618, an amplifier 608, and a speaker 610. The memory, the sensor input 612/618, and the amplifier 608 are operationally related to the microcontroller 602. Speaker 610 is operationally related to amplifier 608. The plushy 400 comprises the electronic control system 600. The method then moves to step 1006.

In step 1006, each time the patient feels the onset of one of the social or emotional conditions 804, at least one of the instructive messages 806 is played by way of the speaker 610 when patient 302 triggers appropriate one or more of the sensor inputs 612/618. Each of the instructive messages 806 is associated with one or more of the sensor inputs 612/618. The method then moves to step 1008.

In step 1008, the social or emotional condition is mitigated by patient 302 listening to the instructive message 806 and physically implementing the self-soothing skill taught by the instructive message 806. The method is then exited.

In an exemplary embodiment that can be interchangeably used with the methods of the present invention, in step 1204, the patient treatment plan 802 can be conducted over a treatment period until responsive to the onset of the social or emotional condition 804 in patient 302, patient 302 physically implements the self-soothing skill, mitigating the social or emotional condition 804, in the absence of patient 302 interacting with the plushy 400.

In an exemplary embodiment, such a treatment period can range from days to weeks to years depending on the nature of the social or emotional conditions 804, the interaction time between patient 302 and plushy 400, and other factors.

In an exemplary embodiment that can be interchangeably used with the methods of the present invention, in step 1206, at least one situational message 810 that can be selected and recorded or downloaded by a caregiver 306 is encoded 816 in the memory 614, wherein the situational message 810 relates to the situational environment around patient 302.

Figure 3:
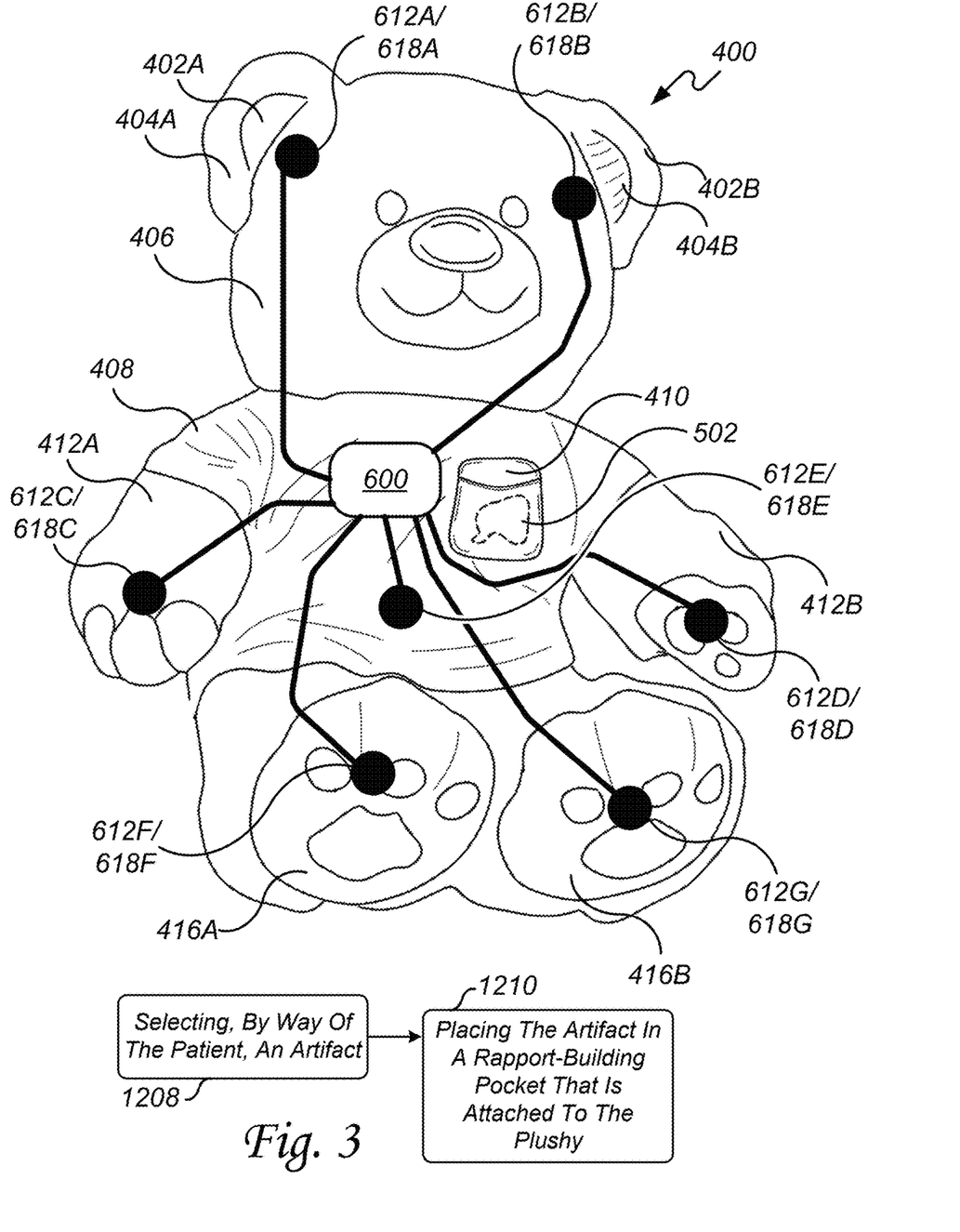
FIG. 3 illustrates one example of a plushy interactive device.

Referring to FIG. 3, there is illustrated one example of a plushy 400 interactive device. In an exemplary embodiment, a plushy 400 can be a soft plush toy that comprises an electronic control system 600. Distributed to plushy 400 extremities 406/412A-B/416A-B and/or other places can be more than one input sensor 612A-G/618A-G. The input sensors 612A-G/618A-G are interconnected with and operationally related to microcontroller 602 which is part of the electronic control system 600. In a plurality of exemplary embodiments, any number of input sensors 612/618 can be implemented and used as may be required and/or desired in a particular embodiment.

In operation, triggering one of the input sensors 612A-G/618A-G causes one of the instructive messages 806, situational messages 810, or therapist messages 812 to be played by way of speaker 610.

In the present invention, an advantage is that part of the patient treatment plan 802 can be a rapport-building method or step between patient 302 and plushy 400. In this regard, the plushy 400 can be dressed in clothes 408 such as a shirt, pants, and/or other types and kinds of clothes. Such clothing can comprise a pocket 410 wherein patient 302 can select an artifact 510 of personal meaning and place it in pocket 410. Such an artifact 502 can be a simple object that has meaning to patient 302. By placing artifact 510 in pocket 410, patient 302 creates a rapport or emotional bond between patient 302 and plushy 400. Such rapport-building pocket 410 can be located in clothing placed on plushy 400 or it can be a pocket integrally formed into plushy 400 that is open and closable by patient 302. Such artifacts can be for example and not a limitation, a coin, a toy, a picture, a rock, a treasure, an article of clothing, or countless other things patient 302 could select.

In operation, a rapport-building pocket 410 can be attached to plushy 400, wherein the patient treatment plan 802 comprises patient 302 selecting artifact 502 and placing artifact 502 into rapport-building pocket 410 to form an emotional bond with plushy 400. Such an emotional bonding step helps patient 302 develop a trusting relationship and emotional connection with plushy 400 which aids in the effectiveness of implementing the patient treatment plan 802 and how instructive messages 806, situational messages 810, or therapist messages 812 are received and acted upon by patient 302.

In an exemplary embodiment that can be interchangeably used with the methods of the present invention, in step 1208, patient 302 can select artifact 502, wherein artifact 502 is an object that has meaning to the patient. The method then moves to step 1210.

In step 1210, artifact 502 is placed in a rapport-building pocket 410 that is attached to the plushy 400, wherein the patient treatment plan 802 comprises the patient selecting artifact 502 and placing artifact 502 into the rapport-building pocket 410 to form an emotional bond with the plushy 400.

In an exemplary embodiment, plushy 400 can be constructed with different kinds of fabric material to create a unique touch sensation for patient 302. As an example, the ears 404A-B can be lined with a silky material 402A in one ear and a coarser material 402B in the other ear. Having different touch sensation areas on plushy 400 can aid patient 302 by drawing their touch sensation to different areas of plushy 400.

In other exemplary embodiments, other areas of the plushy 400 can be configured with different kinds of materials to create unique touch areas that aid patient 302 treatment as may be required and/or desired in a particular embodiment.

Referring to FIG. 4, there is illustrated one example of a system of teaching social and emotional management skills to a patient 302. In a plurality of exemplary embodiments, features of the remote data processing resource 202, the computing devices 212, and the electronic control system 600 can be configured as may be required and/or desired in a particular embodiment including excluding a feature that is not needed for a particular embodiment. As an example, and not a limitation, should the electronic control system 600, in a particular embodiment, not require a camera 616 then the camera 616 can be excluded from the configuration for that embodiment.

In an exemplary embodiment, one or more of the electronic control system 600 can be integrated into plushy 400, clothing worn by plushy 400, a combination of both, or integrated into plushy in other suitable ways. In addition, the electronic control system 600 can be a web-enabled control system 600.

The term "web-enabled", "web-enabled control system", or "web-enabled control system 600" in the present invention is intended to mean an Internet-of-Things (IoT) device. In this regard, a device that is capable of connecting a physical device such as the plushy 400 to the digital world. Stated differently, web-enabling is equipping a device such as plushy 400 with the necessary electronics and software to be monitored, controlled, receive and store data including but not limited to instructive, situational, and therapist messages for playback, and data communication locally and/or remotely with other data communicating devices. Such other data-communicating devices can be referred to as computing devices 212A-C or computing devices 212 and include smartphones, smartwatches, tablets, laptops, desktop computers, mobile computing devices, other web-enabled devices, servers, and other similar or suitable devices.

In an exemplary embodiment, computing devices 212A-C can data communicate with the remote data processing resources 202, and utilize data storage resources 206A.

Remote data processing resources 202 can be a server or other types and kinds of data processing resources. Furthermore, computing devices 212A-C, remote data processing resources 202, data storage resources 206A-B, a web-enabled electronic control system 600, and other types and kinds of data communicating devices, remote data processing resources, and electronic control systems 600 can data communicate over a global network 214. The Internet is a global network 214.

In an exemplary embodiment, a remote data processing resource 202 can comprise a microprocessor 204A, a database 206A, a memory 208A, and a plurality of communication interface 210A. The database 206A, memory 208A, and the plurality of communication interface 210A are operationally related to the microprocessor 204A.

The microprocessor 204A can be INTEL, ZILOG, MICROCHIP, AMD, ARM, and/or other types or kinds of microprocessors.

The memory 208A can be a combination of RAM, ROM, flash, hard drives, solid-state drives, USB flash drives, and/or other types and kinds of memory.

The plurality of communication interface 210A can be LAN, WAN, USB, Ethernet, RS232, RS485, serial, WiFi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

The database 206A is not particularly limited and can be MYSQL, SQL, ORACLE, MYMARIA, or other types and/or kinds of databases as may be required and/or desired in a particular embodiment.

The remote data processing resource 202 is not particularly limited in choice of operating systems or hosting requirements or configurations. As such, remote data processing resource 202 can be LINUX BASED, MICROSOFT BASED, AMAZON WEB SERVICES (AWS) BASED, MICROSOFT AZURE BASED, or use other types and kinds of operating systems and hosting configurations, as may be required and/or desired in a particular embodiment.

In an exemplary embodiment, a computing device 212 can comprise a microprocessor 204B, a database 206B, a memory 208B, a plurality of communication interfaces 210B, a display 218, and general purpose inputs and outputs (GPIO) 220. The database 206B, memory 208B, the plurality of communication interfaces 210B, display 218, and GPIO 220 are operationally related to the microprocessor 204B.

The microprocessor 204B can be INTEL, ZILOG, MICROCHIP, AMD, ARM, and/or other types or kinds of microprocessors.

The memory 208B can be a combination of RAM, ROM, flash, hard drives, solid-state drives, USB flash drives, and/or other types and kinds of memory.

The plurality of communication interfaces 210B can be LAN, WAN, USB, Ethernet, RS232, RS485, serial, WiFi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

In an exemplary embodiment, a computing device 212B can data communicate directly 216 with the plushy 400 by way of the embedded web-enabled electronic control system 600, such as by Bluetooth or other suitable protocols and methods, or data communicate remotely over the global network 214 with the plushy 400. Such data communications can be facilitated by a software application that runs on computing device 212B or by way of other suitable methods.

In an exemplary embodiment, the web-enabled electronic control system 600, remote data processing resource 202, and computing devices 212A-C can all data communicate with each other by way of the global network 214.

Display 218 can be an LCD, OLED, LED, as well as have touch input capabilities and/or other types and kinds of displays and user inputs as may be required and/or desired in a particular embodiment.

The GPIO 220 can be TTL, CMOS, transistors, buffers, relays, pushbuttons, switches, and/or other types and kinds of GPIO circuits.

The database 206B is not particularly limited and can be MYSQL, SQL, ORACLE, MYMARIA, MSACCESS, or other types and/or kinds of databases as may be required and/or desired in a particular embodiment.

The computing device 212 is not particularly limited in choice of operating systems or hosting requirements or configurations. As such, computing devices 212 can be LINUX BASED, MICROSOFT BASED, APPLE IOS, or use other types and kinds of operating systems as may be required and/or desired in a particular embodiment.

In an exemplary embodiment, the computing device can run a software application that provides connectivity and interactive functionality between the therapist 304, caregiver 306, other authorized persons, remote data processor 202, and plushy 400 as may be required and/or desired in a particular embodiment.

In an exemplary embodiment, the plushy 400 can be equipped with one or more of a web-enabled control system 600. Such a web-enabled control system can comprise a microcontroller 602 which is operationally related to a plurality of communication interfaces 604, a power supply 606, an amplifier 608, general-purpose inputs and outputs (GPIO) 612, a memory 614, a camera 616, sensors 618, a microphone 620, and ambient sensors 622.

The microcontroller 602 can be INTEL, ZILOG, MICROCHIP, AMD, ARM, and/or other types or kinds of microcontrollers.

The memory 614 can be a combination of RAM, ROM, flash, hard drives, solid-state drives, USB flash drives, permanent or removable, and/or other types and kinds of memory.

The plurality of communication interfaces 604 can be LAN, WAN, USB, Ethernet, RS232, RS485, serial, WiFi, 802.11abgn and similar, 2G 3G 4G 5G compatible, Bluetooth, TCP, UDP, Mesh Network, Zigbee, Pico Network, LORAN, and/or other types and kinds of communication interfaces and protocols.

In an exemplary embodiment, the communication interface 604 is operationally related to the microcontroller 602. The electronic control system 600 by way of the communication interface 604 data communicates with the remote data processing resource 202, and data computing devices 212 in a local area network environment and/or a wide area network environment across a global network 214 in a wired or wireless manner as may be required and or desired in a particular embodiment. The Internet is a global network 214.

In an exemplary embodiment, by way of the communication interface 604 the electronic control system 600 can data communicates with the remote data processing resource 202, and in accordance with the patient treatment plan 806 at least one of the interactive messages can be downloaded from the remote data processing resource and encoded in the memory 614, and/or at least one of a patient plushy interaction metric can be data communicated to the remote data processing resource 202. In this regard, such patient plushy interaction metric can include, for example and not a limitation, how many times the plushy 400 and patient 302 interacted, which input sensors 612/618 were used by patient 302, when and where, and how many times, and other metrics and data as may be required and/or desired in a particular embodiment.

In another exemplary embodiment, by way of the communication interface 604 the electronic control system 600 data communicate with the remote data process resource 202 or a computing device 212 when patient 302 triggers one of the sensor inputs 612/618. In this regard, the plushy 400 can be configured to report by data communication each time patient 302 interacts with plushy 400 initiating one of the instructive messages 806 to be played by triggering one of the input sensors 612/618.

The power supply 606 can be AC, DC, battery, rechargeable battery, solar, and/or other types and kinds of power supplies.

The amplifier 608 isn't particularly limited and can be any suitable type of amplifier as may be required and/or desired in a particular embodiment. Speaker 610 is operationally related to the amplifier 608 and isn't particularly limited. Speaker 610 can be any suitable type of speaker as may be required and/or desired in a particular embodiment.

The GPIO 612 can be TTL, CMOS, transistors, buffers, relays, pushbuttons, switches, and/or other types and kinds of GPIO circuits.

The camera 616 isn't particularly limited and can be any suitable type of camera as may be required and/or desired in a particular embodiment.

The sensors 618 can be PIR motion sensors, infrared, thermal, Doppler radar, ultrasonic, capacitance, touch-type, optical, Hall effect, switch, fingerprint, and other types of biometric sensors, and/or other types and kinds of sensors. In an exemplary embodiment, analog-type sensor determinations can be converted to digital values so that the microcontroller 602 can process the data. Alternatively, the microcontroller 602 can perform analog-to-digital conversions if equipped to perform such functions.

The microphone 620 isn't particularly limited and can be any suitable type of microphone as may be required and/or desired in a particular embodiment.

The ambient condition sensors 622 can be temperature, moisture, humidity, sunlight, time, date, and/or other types and kinds of sensors. In an exemplary embodiment, analog-type sensor determinations can be converted to digital values so that the microcontroller 602 can process the data. Alternatively, the microcontroller 602 can perform analog-to-digital conversions if equipped to perform such functions.

Figure 5:
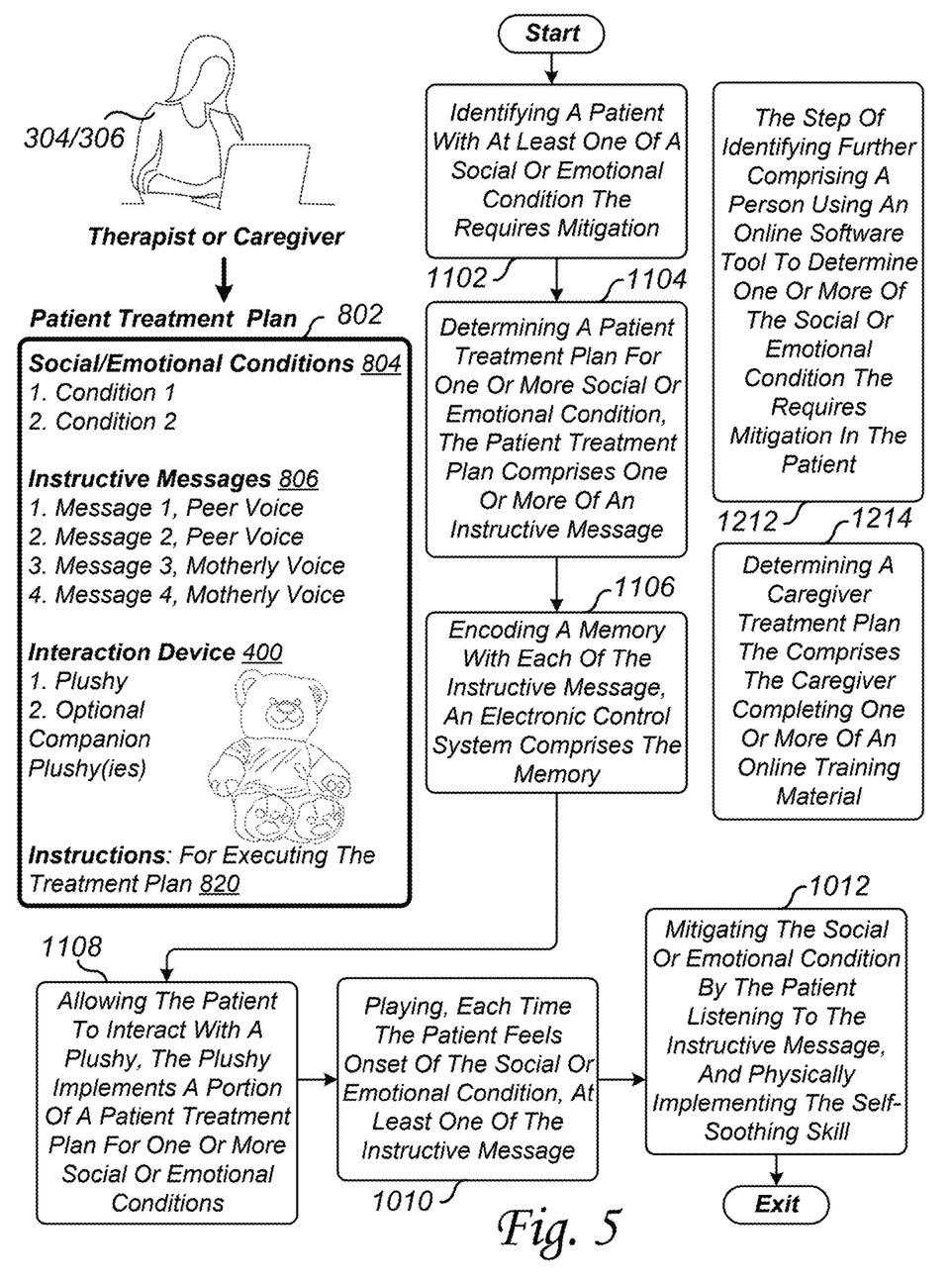
FIG. 5 illustrates one example of a therapeutic method for teaching social and emotional management skills to a patient.

Referring to FIG. 5, there is illustrated one example of a method of teaching social and emotional management skills to a patient. In an exemplary embodiment, a therapist 304 and/or a caregiver 306 can create, determine, effectuate, or otherwise implement a patient treatment plan 802. Such patient treatment plans 802 can be predetermined by a therapist 304 and/or a caregiver 306 for certain commonly occurring social or emotional conditions 804, or patient treatment plans 802 can be customized by a therapist 304 and/or a caregiver 306 based on the unique needs of a patient.

For those cases in which a predetermined patient treatment plan 802 is appropriate for patient 302, the patient treatment plan 802 including the plushy 400 encoded with the appropriate instructive messages 806 can be purchased (including from a website) or otherwise obtained or provisioned to the caregiver 306 and/or patient 302. Once received the patient treatment plan 802 can commence and patient 302 can begin interacting with plushy 400.

For those cases in which a predetermined patient treatment plan 802 is not appropriate for patient 302, the treatment plan 802 including the plushy 400 can be purchased (including from a website) or otherwise obtained or provisioned to the caregiver 306 and/or patient 302 however, prior to patient 302 interacting with plushy 400 selection of the instructive messages 806 based in part on the identified social or emotional conditions 804 must be selected and encoded in memory 614 thus customizing plushy 400 for the specific patient needs.

Additionally, in an exemplary embodiment, one or more companion plushy 400 can be purchased (including from a website) obtained or otherwise provisioned to the caregiver 306 or other authorized persons for use by other persons than the patient 302 such as siblings, friends, and other people. The companion plushy 400 is designed to complement and enhance the patient treatment plan 802 by allowing those close to patient 302 to also interact with the companion plushy 400 which is encoded with instructive messages 806 that address patient 302 treatment needs not the person in possession of the companion plushy 400. This creates the opportunity for more and different instructive messages 806 for patient 302 to engage with including while playing with people in possession of the companion plushy 400.

In operation, the patient treatment plan 802 can comprise the use of one or more companion plushy 400 to be used by people close to patient 302 such as family, friends, and other people. Companion plushy 400 allows siblings or friends of patient 302 to interact with the companion plushy 400. Each of the companion plushy 400 comprises the electronic control system 600 in which memory 614 is encoded with one or more of the instructive messages 806, and at least some of the instructive messages 806 in the companion plushy 400 are different from the instructive messages 806 in the plushy 400. The instructive messages 806 in the companion plushy 400 are selected to counteract at least one of the identified social or emotional conditions 804 that patient 302 is being treated for.

While each model of plushy 400 comprises instructive messages 806, certain models of plushy 400 can be equipped to allow a caregiver 306 or other authorized persons to select and record or otherwise encode in memory 614 with one or more situational messages 810.

Additionally, while each model of plushy 400 comprises instructive messages 806, certain models of plushy 400 can be equipped to allow a therapist 304 or other authorized persons to select and record or otherwise encode in memory 614 one or more therapist messages 812.

The method begins in step 1102, by identifying that patient 302 has at least one of the social or emotional conditions 804 that requires mitigation. Such a determination can be made by a therapist or other qualified and/or authorized persons.

In this regard, in an exemplary embodiment that can be interchangeably used with the methods of the present invention, in step 1212, identifying in step 1102 can further comprise a person such as a caregiver 306, patient 302, or other authorized person using an online software tool to determine one or more of the social or emotional condition 804 that requires mitigation in the patient 302. Such an online software tool can be a questionnaire, a frequently asked question (FAQ) webpage, a telemedicine or teletherapy session with a therapist or other authorized person, an informational blog, audio, podcasts, videos, or other online software tools as may be required and/or desired in a particular embodiment. The method then moves to step 1104.

In step 1104, a patient treatment plan 802 is determined for one or more of the social or emotional conditions 804 identified. The patient treatment plan comprises one or more instructive messages 806 selected based in part on a self-soothing skill desired to counteract at least one of the identified social or emotional conditions 804. The instructive message 806 teaches the self-soothing skill that patient 302 physically implements. The method then moves to step 1106.

In step 1106, a memory 614 is encoded with each of the instructive messages 806. An electronic control system 600 comprises a microcontroller 602, the memory 614, one or more sensor inputs 612/618, an amplifier 608, and a speaker 610. The memory 614, the sensor input 612/618, and the amplifier 608 are operationally related to the microcontroller 602. Speaker 610 is operationally related to amplifier 608. The method then moves to step 1108.

In step 1108, patient 302 is allowed to interact with a plushy 400. The plushy 400 implements a portion of the patient treatment plan 802 for one or more of the social or emotional conditions 804 identified as patient 302 interacts with the plushy 400. The plushy 400 comprises the electronic control system 600. The method then moves to step 1110.

In step 1110, each time patient 302 feels the onset of one of the social or emotional conditions 804, at least one of the instructive messages 806 is played by way of speaker 610 when patient 302 triggers the appropriate sensor inputs 612/618. Each of the instructive messages 806 is associated with one or more of the sensor inputs 612/618. The method then moves to step 1112.

In step 1112, the social or emotional conditions 804 are mitigated, by patient 302 listening to the instructive message 806 and physically implementing the self-soothing skill taught by the instructive message 806. The method is then exited.

In an exemplary embodiment that can be interchangeably used with the methods of the present invention, in step 1214, a caregiver treatment plan is determined that comprises the caregiver 306 completing one or more of online training material. Wherein the caregiver treatment plan teaches caregiver 306 how to implement the patient treatment plan 802, use the plushy 400 in connection with mitigating the social or emotional condition 804, monitor the progress of patient 302 during the patient treatment plan 802, and interact with the patient 302 as the patient 302 interacts with the plushy 400.

The capabilities of the present invention can be implemented in software, firmware, hardware, or some combination thereof.

As one example, one or more aspects of the present invention can be included in an article of manufacture (e.g., one or more computer program products) having, for instance, computer-usable media. The media has embodied therein, for instance, computer-readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A therapeutic system for teaching social and emotional management skills to a patient, the system comprising:
a patient plushy, the patient plushy having a first electronic control system integrated therein, the patient plushy comprising a first body, a first head, and one or more first extremities, the first electronic control system comprising a first microcontroller, a first memory, a first amplifier, a first speaker, and a first plurality of sensors located in the first body, the first head, and the one or more first extremities of the patient plushy;
wherein the first memory, the first plurality of sensors, and the first amplifier are operationally connected to the first microcontroller, and the first speaker is operationally connected to the first amplifier;
wherein the first memory of the patient plushy stores one or more instructive messages that are associated with a patient treatment plan for one or more social or emotional conditions, the one or more instructive messages being configured to teach one or more self-soothing skills that the patient physically implements, each of the one or more instructive messages being associated with particular sensors of the first plurality of sensors;
wherein the patient plushy receives a sensor input from the patient from one or more of the first plurality of sensors, indicating that the patient feels the onset of at least one of the one or more of the social or emotional conditions and, upon receiving the sensor input, the patient plushy accesses and selects, in accordance with the patient treatment plan, at least one of the one or more instructive messages, the one or more instructive messages being selected based, in part, on the one or more self-soothing skills desired to counteract at least one of the one or more social or emotional conditions;
wherein, upon selection of the one or more instructive messages, the selected one or more instructive messages is amplified by the first amplifier and outputted by the first speaker, instructing the patient to perform one or more of the one or more self-soothing skills;
wherein treatment continues over a treatment period until, responsive to the onset of the one or more social or emotional conditions in the patient, the patient physically implements the one or more self-soothing skills, mitigating the one or more social or emotional conditions in the absence of the patient interacting with the patient plushy;
wherein, in a portion of the patient treatment plan, the therapeutic system further comprises the use of one or more companion plushy, each of the one or more companion plushy having a second electronic control system integrated therein, the one or more companion plushy comprising a second body, a second head, and one or more second extremities, the second electronic control system of the one or more companion plushy comprising a second microcontroller, a second memory, a second amplifier, a second speaker, and a second plurality of sensors located in the second body, the second head, and the one or more second extremities of the one or more companion plushy;

wherein the second memory of the one or more companion plushy receives and stores one or more companion instructive messages that are associated with the patient treatment plan, at least some of the one or more companion instructive messages are different from the one or more instructive messages, the one or more companion instructive messages being selected to counteract at least one of the one or more social or emotional conditions for which the patient is being treated, the one or more companion instructive messages being amplified by the second amplifier and outputted by the second speaker of the one or more companion plushy.

2. The therapeutic system in accordance with claim 1, the one or more social or emotional conditions is at least one of the following: anger, fear, anxiety, depression, disruptive behavior, dissocial disorder, or post-traumatic stress disorder.

3. The therapeutic system in accordance with claim 1, the one or more self-soothing skills include one or more of the following: instructing the patient to look around a room and describe what they see, hear, smell, or feel, instructing the patient to find something in the room to smell or touch, instructing the patient to sniff an imaginary flower or blow up an imaginary balloon, or instructing the patient to perform a deep breathing exercise.

4. The therapeutic system in accordance with claim 1, further comprising:

an artifact, wherein the artifact is an object that has meaning to the patient; and a rapport-building pocket that is attached to the patient plushy, wherein the patient treatment plan comprises the patient selecting the artifact and placing the artifact into the rapport-building pocket to form an emotional bond with the patient plushy.

5. The therapeutic system in accordance with claim 1, wherein:

at least one of the one or more instructive messages is recorded or downloaded in a peer voice by someone of similar age as the patient; or at least one of the one or more instructive messages is recorded or downloaded in a motherly voice by an adult female or a fatherly voice by an adult male.

6. The therapeutic system in accordance with claim 1, wherein at least one of the one or more instructive messages is a situational message that is selected and recorded or downloaded and is changeable by a caregiver, wherein the situational message relates to the situational environment around the patient.

7. The therapeutic system in accordance with claim 1, wherein, upon completion of the one or more self-soothing skills, the patient plushy communicates an interaction metric indicating the number of times the patient plushy and patient interacted.

8. The therapeutic system in accordance with claim 1, further comprising:

one or more therapy session messages, the first memory is encoded with each of the one or more therapy session messages and played by way of the first speaker only during a therapy session between a therapist and the patient when the patient triggers one of the sensor input, the one or more therapy session messages instruct the patient to teach one or more of the one or more self-soothing skills to the patient plushy so that the therapist can evaluate treatment progress of the patient.

9. The therapeutic system in accordance with claim 1, further comprising:

a caregiver treatment plan, the caregiver treatment plan teaches the caregiver how to implement the patient treatment plan, use the patient plushy in connection with mitigating the one or more social or emotional conditions, monitoring progress of the patient during the patient treatment plan, and interacting with the patient as the patient interacts with the patient plushy.

10. The therapeutic system in accordance with claim 1, further comprising:

one or more remote data processing resources, the first electronic control system comprises a communication interface, by way of the communication interface the electronic control system data communicates with the one or more remote data processing resources, in accordance with the patient treatment plan, at least one of the one or more interactive messages is downloaded from the one or more remote data processing resources and encoded in the first memory.

11. The therapeutic system in accordance with claim 1, further comprising:

at least one computing device; and one or more remote data processing resources, the first electronic control system comprises a communication interface, by way of the communication interface the first electronic control system data communicates with the one or more remote data process resources or a computing device when the patient triggers one of the sensor input.

12. A method implemented at least in part by the therapeutic system of claim 1, the method comprising the steps of:

providing the therapeutic system;

encoding the first memory with each of the one or more instructive messages;

playing, by the first speaker via the first amplifier of the patient plushy each time the patient feels the onset of one of the one or more social or emotional conditions, at least one of the one or more instructive messages; and causing the patient plushy to implement the patient treatment plan to mitigate the one or more social or emotional conditions by way of the patient listening to one or more instructive messages, and physically implementing the one or more self-soothing skills taught by the one or more instructive messages.

13. The method in accordance with claim 12, wherein the one or more self-soothing skills include one or more of the following: instructing the patient to look around a room and describe what they see, hear, smell, or feel, instructing the patient to find something in the room to smell or touch, instructing the patient to sniff an imaginary flower or blow up an imaginary balloon, or instructing the patient to perform a deep breathing exercise.

14. The method in accordance with claim 12, further comprising the steps of:

selecting, by way of the patient, an artifact, wherein the artifact is an object that has meaning to the patient; and placing the artifact in a rapport-building pocket that is attached to the patient plushy, wherein the patient treatment plan comprises the patient selecting the artifact and placing the artifact into the rapport-building pocket to form an emotional bond with the patient plushy.

15. The method in accordance with claim 12, further comprising the step of:
    conducting a therapy session between a therapist and the patient, the first memory is encoded with one or more therapy session messages and played by way of the first speaker only during the therapy session when the patient triggers one of the sensor input, the one or more therapy session messages instruct the patient to teach one or more of the one or more self-soothing skills to the patient plushy so that the therapist can evaluate treatment progress of the patient.

16. A method implemented at least in part by the therapeutic system of claim 1, the method comprising the steps of:
    providing the therapeutic system;
    diagnosing the patient with one or more social or emotional conditions that require mitigation;
    determining the patient treatment plan for the one or more social or emotional conditions; and
    encoding the first memory with the one or more instructive messages that are selected based on the one or more social or emotional conditions; and
    causing the patient plushy to implement the patient treatment plan to mitigate the one or more social or emotional conditions, by the patient listening to the instructive message and physically implementing the self-soothing skill taught by the one or more instructive messages.

17. The method in accordance with claim 16, wherein the one or more self-soothing skills include one or more of the following: instructing the patient to look around a room and describe what they see, hear, smell, or feel, instructing the patient to find something in the room to smell or touch, instructing the patient to sniff an imaginary flower or blow up an imaginary balloon, or instructing the patient to perform a deep breathing exercise.

18. The method in accordance with claim 16, wherein the therapeutic system further comprises an online software tool configured to receive input from a person to determine the one or more social or emotional conditions that require mitigation in the patient and wherein the method further comprises receiving, by the online tool, the input from a person to determine the one or more social or emotional conditions that require mitigation in the patient and formulating the treatment plan using this information.

19. The method in accordance with claim 16, further comprising the step of:
    determining a caregiver treatment plan that comprises the caregiver completing one or more of an online training material, wherein the caregiver treatment plan teaches the caregiver how to implement the patient treatment plan, use the patient plushy in connection with mitigating the one or more social or emotional conditions, monitoring progress of the patient during the patient treatment plan, and interacting with the patient as the patient interacts with the patient plushy.

20. The method in accordance with claim 16, further comprising the step of:
    conducting a therapy session between a therapist and the patient, the first memory is encoded with one or more therapy session messages and played by way of the first speaker only during the therapy session when the patient triggers one of the sensor input, the one or more therapy session messages instruct the patient to teach one or more of the one or more self-soothing skills to the patient plushy so that the therapist can evaluate treatment progress of the patient.

21. The method in accordance with claim 16, further comprising the step of:
    encoding in the first memory with at least one situational message that is selected and recorded or downloaded by a caregiver, wherein the at least one situational message relates to the situational environment around the patient, the at least one situational message is changeable by the caregiver.

* * * * *